United States Patent
Pallikaris et al.

(10) Patent No.: US 6,723,089 B2
(45) Date of Patent: Apr. 20, 2004

(54) DEVICE FOR THE SHAPING OF A SUBSTANCE ON THE SURFACE OF A CORNEA

(75) Inventors: Ioannis Pallikaris, Kalessa (GR); Harilaos Ginis, Heraklion (GR)

(73) Assignee: Ioannis Pallikaris, Heraklion (GR)

( * ) Notice: Subject to any disclaimer, the term of this patent is extended or adjusted under 35 U.S.C. 154(b) by 0 days.

(21) Appl. No.: 09/839,640

(22) Filed: Apr. 20, 2001

(65) Prior Publication Data

US 2002/0052596 A1 May 2, 2002

(51) Int. Cl.$^7$ .................................. A61B 18/18
(52) U.S. Cl. ........................ 606/5; 351/212; 351/219; 623/5.11; 623/5.12; 623/5.16; 606/27
(58) Field of Search ................... 351/212, 219; 623/5.11, 5.12, 5.16; 606/5.27

(56) References Cited

U.S. PATENT DOCUMENTS

| | | | | |
|---|---|---|---|---|
| 4,619,662 A | * | 10/1986 | Juergens, Jr. | 264/1.7 |
| 4,840,754 A | * | 6/1989 | Morgan | 264/2.2 |
| 4,856,513 A | * | 8/1989 | Muller | 606/5 |
| 5,196,027 A | * | 3/1993 | Thompson et al. | 128/898 |
| 5,277,911 A | * | 1/1994 | Viegas et al. | 424/427 |
| 5,279,611 A | | 1/1994 | McDonnell et al. | |
| 5,332,802 A | * | 7/1994 | Kelman et al. | 530/356 |
| 5,492,135 A | | 2/1996 | DeVore et al. | |
| 5,674,283 A | * | 10/1997 | Stoy | 623/5.11 |
| 5,716,633 A | * | 2/1998 | Civerchia | 264/1.1 |
| 5,779,696 A | * | 7/1998 | Berry et al. | 606/16 |
| 5,807,381 A | | 9/1998 | Lieberman | |
| 5,975,875 A | * | 11/1999 | Crowe et al. | 425/215 |
| 6,074,579 A | * | 6/2000 | Greshes | 264/1.32 |
| 6,132,735 A | * | 10/2000 | Harris et al. | 424/400 |
| 6,416,179 B1 | * | 7/2002 | Lieberman et al. | 351/212 |
| 6,589,558 B1 | * | 7/2003 | Pallikaris | 424/468 |

OTHER PUBLICATIONS

Ioannis G. Pallikaris, MD, Maria E. Papatzanaki, MD, Evdoxia Z. Stathi, MD, Oliver Frenschock, and Anthimos Georgiadis, PhD, *Laser in Situ Keratomileusis*, Lasers in Surgery and Medicine, vol. 10 pp. 463–468, 1990.

Stephen L. Trokel, M.D., R. Srinivasan, PhD., and Bodil Baren, B.A., *Excimer Laser Surgery of the Cornea*, vol. 96, No. 6, pp. 710–715, 1983.

David S. Gartry, FRCS, FCOphth, Malcolm G. Kerr Muir, FRCS, FCOphth, John Marshall, PhD., *Photorefractive Keratectomy with an Argon Fluoride Excimer Laser: A Clinical Study*, vol. 7, pp. 420–435, Nov./Dec. 1991.

Terry J. Van Der Werff, D.Phil., *A New Single–Parameter Ocular Rigidity Function*, 1981, vol. 92, pp. 391–395.

Winston Roberts, M.D., and J. William Rogers, M.D., *Postural Effects on Pressure and Ocular Rigidity Measurements*, pp. 111–118.

Peter P. Purslow, Phd, Wojciech S.S. Karwatowski, FROCOphth, *Ocular Elasticity*, pp. 1686–1692.

Joseph N. Simone, MD and Marc M. Whitacre, MD, *The Effect of Intraocular Gas and Fluid Volumes on Intraocular Pressure*, Ophthalmology, Feb. 1990, vol. 97, No. 2, pp. 238–243.

(List continued on next page.)

*Primary Examiner*—Henry Bennett
*Assistant Examiner*—Kathryn Odland
(74) *Attorney, Agent, or Firm*—Brinks Hofer Gilson & Lione

(57) ABSTRACT

A device for helping to correct imperfections of a cornea includes a molding lens. The molding lens includes an external surface having a concave shape to correspond to the desired shape of the cornea. Heating and cooling elements are located with the molding lens to control the temperature the molding lens, and thus to control the temperature of a substance located on the molding lens.

15 Claims, 3 Drawing Sheets

OTHER PUBLICATIONS

John E. Eisenlohr, M.E. Langham and A.E. Maumenee, *Manometric Studies of the Pressure–Volume Relationship in Living and Enucleated Eyes of Individual Human Subjects*, Brit. J. Ophthal., 1992, vol. 46, pp. 536–548.

Richard F. Brubaker, *Kinds and Properties of Tonometers*, Clinical Opthalmology, vol. 3, Chap. 47, pp. 1–7.

Jonas S. Friedenwald, M.D., *Tonometer Calibration, An Attempt to Remove Discrepancies Found in the 1954 Calibration Scale for Schoitz Tonometers*, Jan.–Feb. 1957, pp. 108–123.

Carsten Edmund, *Corneal Elasticity and Ocular Rigidity in Normal and Keratoconic Eyes*, Acta Ophthalmologica, 1988, vol. 66, pp. 134–140.

Ephraim Friedman, MD, Sara Krupsky, MD, Anne Marie Lane, MPH, Setsuko S. Oak, Eric S. Friedman, MD, Kathleen Egan, MPH, Evangelos S. Gragoudas, MD, *Ocular Blood Flow Velocity in Age–Related Macular Degeneration*, Ophthalmology, vol. 102, No. 4, Apr. 1995, pp. 640–646.

Mark W Johnson, MD, Dennis P. Han, MD, Kenneth E. Hoffman, MS, *The Effect of Scleral Buckling on Ocular Rigidity*, Ophthalmology 1990, vol. 97, pp. 190–195.

Evangelos S. Gragoudas, MD, Suresh R. Chandra, MD, Ephraim Friedman, MD, Michael L. Klein, MD, Micael Van Buskirk, MD, *Disciform Degeneration of the Macula*, Arch Ophthalmol, vol. 94, May 1976, pp. 755–757.

Ephraim Freidman, MD, *A Hemodynamic Model of the Pathogenesis of Age Related Macular Degeneration*, pp. 1–14.

* cited by examiner

DEVICE FOR THE SHAPING OF A SUBSTANCE ON THE SURFACE OF A CORNEA

REFERENCE TO EARLIER FILED APPLICATION

The present application claims the benefit of Greek Application No. 20000100144, filed Apr. 21, 2000, which is incorporated by reference herein.

BACKGROUND

Different types of known modulators for shaping the cornea of an eye have been proposed for refractive surgery. Widely used is a modulator from photoabltable polymer that is placed in the optical path of a transportation system of a laser beam. This type of modulator, which has the shape of a spherical or of a toroidal lens is used for the correction of the usual refractive irregularities, like myopia or astigmatism. A modulator remote from the eye has the disadvantage, however, of correcting only simple and predefined refractive irregularities of the eye.

It is also known to cover of the corneal surface, just before irradiation, with a solution of collagen which solidifies immediatelly after its placement over the cornea. The collagen typically covers the irregularities of the corneal surface. The collagen through the surface forms a relatively smooth external surface. This smooth surface is "projected" finally on the cornea due to the same ablation rate of collagen and the cornea. While this method permits the smoothing of the cornea, it cannot give any prediction for the final shape of the corneal surface especially when the cornea has geometric irregularities of large size compared to the size of the optical zone, for example, irregular astigmatism, scares and dystrophy of the cornea.

Therefore, there exists the need for modulators that can be used in order to correct the surface irregularities of the cornea and at the same time change the shape of the cornea in a way that good optical performance is achieved.

BRIEF SUMMARY

A device includes a molding lens and elements for controlling the temperature of the mold. The molding lens includes an external surface having a concave shape to correspond to the desired shape of the cornea. The device can shape a substance such as hydrogel on the surface of the cornea in the process of developing a photoablatable lenticular modulator for laser irradiation. The temperature of the molding lens can be controlled in various ways. Such ways include circulation of a liquid in the molding lens, supplying an air stream having a controllable temperature on an internal or external surface of the molding lens and contacting the surface of the mold with a heating element.

DETAILED DESCRIPTION

Figure 1:
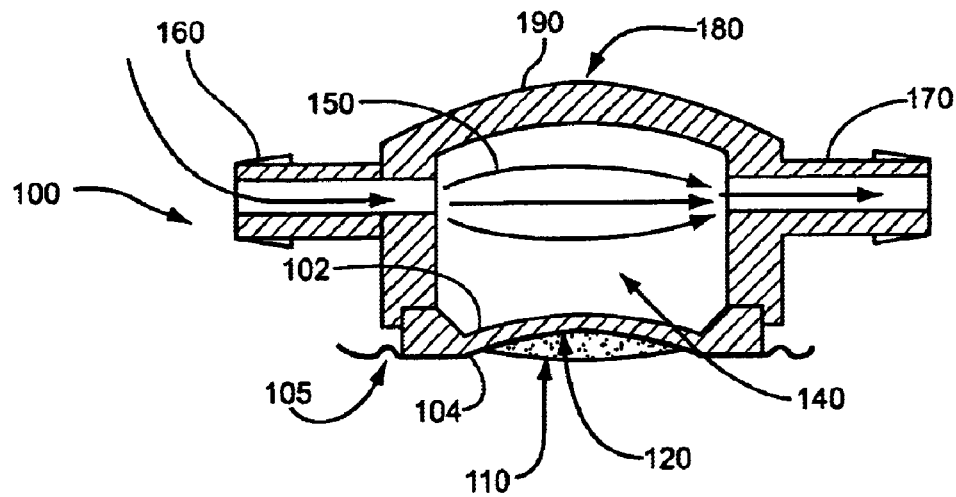
FIG. 1 shows a molding lens according to a preferred embodiment.

Photorefractive surgery is a technique in which the ArF excimer laser is used as a surgical instrument to precisely excise a part of the external surface of corneal tissue from the eye. In addition to the correction of refractive errors (e.g. myopia, astigmatism, and hyperopia), this technique can be applied for the removal of corneal surface opacities and for the elimination of geometric irregularities of the external surface of the corneal tissue.

Typically, the ArF excimer laser is used for the photoablation of the cornea in photorefractive keratectomy or phototherapeutic keratectomy. The laser operates at 193-nm wavelength for the controlled photodecomposition of the corneal tissue. Typical parameters for the operation of such a laser are Energy fluence—100–250 $mJ/cm^2$, pulse repetition rate 20 Hz and pulse duration 20 nsec. The application of excimer lasers in procedures of photodecompotition of the cornea are described in international scientific literature such as Trokel S, Srinivasan R, Braren B. *Excimer Laser surgery of the cornea, Am. J. Ophthalmology* 1983; 94:125, Gartry G S, Kerr Muir M G, Marshall J. *Photorefractive keratectomy with an argon fluoride excimer laser:* a clinical study. J Refractive & Corneal Surgery 1991;7:420–431, and Pallikaris I G, Papatzanaki M, Stathi E, Frenschock O, Georgiadis A, *Laser in situ keratomileusis*. Lasers Surg Med 1990;10:463–468.

The interaction of the laser with the corneal tissue provides accuracy in the ablation depth, efficient photodecomposition and minimal thermal damage of the adjacent tissue.

The laser irradiation is performed with a series of pulses of determined duration, energy and time interval between them. Form variable mechanical diaphragms shape the series of pulses before the pulses strike the cornea. Alternately, the pulses are distributed on the surface of the cornea in a scanning manner or the pulse series undergoes a combination of the above shaping in order to produce a spatial distribution of ablation capable of altering the shape and consequently the optical performance of the cornea. The depth and the width of the ectomy, which determine the aimed correction, are achieved through an adjustment of the irradiation parameters. Irradiation parameters include laser pulse energy, the total number of pulses, diameters and shapes of the mechanical diaphragms, energy fluence (mJ/$cm^2$), pulse frequency (Hz) and the algorithm the modulation and beam scanning.

Normally, after the photodisruption of the surface of the cornea, the tissue remains transparent and has a smooth surface. The smooth surface allows for the tissue reepithelazation with fine optical properties.

In some cases modulators for the irradiation distribution over the cornea surface are used. A modulator includes photoablatable elements that are interposed between the laser beam and the corneal surface. The elements are photoablated during the irradiation, thus permitting the gradual transmission of different sections of the laser beam. When photoablation is concluded, an irradiation pattern is formed repartition that corresponds to the desirable photoablation profile.

FIG. 1 shows a molding lens 100 including an internal surface 102 and an external surface 104. A membrane 105 can be placed on the external surface 104. To correct irregularities of the cornea and change the shape of the cornea, the cornea is covered with a substance 110, such as hydrogel, that includes an equal ablation rate with the cornea. A molding surface 120, for example the external surface 104 of the molding lens 100, shapes the substance 110. Thus, the molding lens 100 gives the desired shape to the substance 110, independently of the initial corneal shape. The molding surface 120 is aligned centrally with the cornea so that the optical axis of the cornea aligns with the axis of symmetry of the molding lens 100.

Greek patent application number 990100250 describes a preferred substance 110 of thermorevesable hydrogel produced by mixing porcine gel, gramineous gel (Carageenan K Type) and coloring substance (Sodium Fluoroscein) that fluoresces in green color if is irradiated by 193 nm Excimer laser. The ablation rate is same of that of the human cornea and its thermorevesibility is based in the property of the rigid hydrogel gel that can be liquefied if is heated suitably and reversibly. The properties of the optical surface of the molds, which are used for the modulation of the initially liquid modulator, have been also identified. Those modulators are shaped over the surface of the cornea under therapy. The inside of the modulator, the side facing the cornea, follows existent geometric irregularities of the cornea and the external side of the modulator includes a well-defined position and shape.

When a thermoreversible hydrogel is used for the preparation of the modulator, the time required for the solidification of the hydrogel depends on various parameters. The parameters includes the initial temperature of the hydrogel, the quantity of the hydrogel, the initial temperature of the mold, the shape of the molding surface 120, the heat capacity of the molding lens 100, the thermal diffusion coefficient of the construction material of the molding surface 100, and the temperature of the room in which the application is taking place. As a result it is not certain that the hydrogel has been solidified entirely at the moment when the molding lens 100 is being removed. It has been also observed that at low temperatures the hydrogel seems to have increased mechanical strength compared to at higher temperatures. Thus, low temperatures allow for easier removal of the mold from the surface of the solidified hydrogel and the risk of destruction is lower than the relatively fragile, at room temperature, layer of the hydrogel.

The molding lens 100 is used for the modulation of the hydrogel on the surface of the cornea. The molding lens 100 is preferably constructed, at least at a central zone, from transparent material, so that the user can observe the cornea and the hydrogel through the mold during the application. The molding lens 100 used for molding the thermoreversible hydrogel can be a composite lens. The molding lens 100 contains defined quantities of a hydrogel to give the layer of the hydrogel desirable geometric characteristics such as radius of curvature and centering, as known to those skilled the art. Molding is performed under defined temperature conditions in order that: a) initially the hydrogel is kept liquid for as long as it is the required for the centering of the molding lens 100. Thereafter, the hydrogel is cooled until solidification occurs in a time interval that is known regardless of external conditions. Then, the removal of the molding lens 100 is attempted when the temperature is sufficiently low, e.g., lower from that of the environment, to facilitate the removal of the molding lens 100.

The molding lens 100 includes the defined shape of the molding surface 120. A temperature of the molding lens 100 is controlled so that the temperature of the layer of the hydrogel that contacts the molding lens 100 is also controlled. In a preferred embodiment the molding lens 100 includes a cavity 140 in which a fluid 150 can circulate. The molding lens 100 can also include an inlet 160 and an outlet 170.

Figure 2:
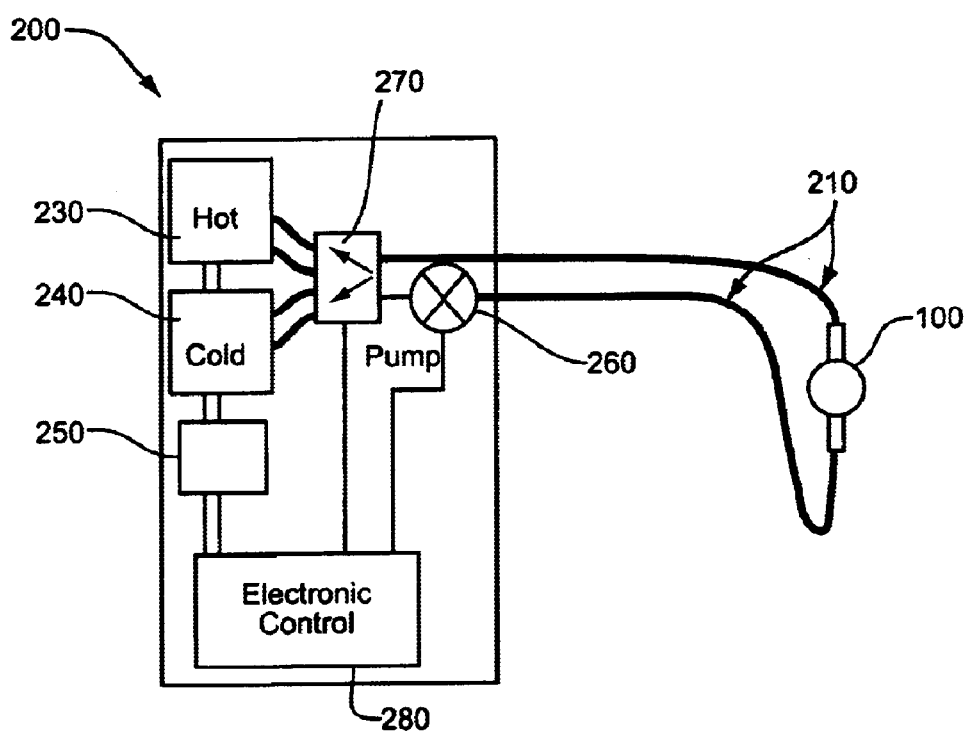
FIG. 2 shows a system for controlling the temperature of the molding lens according to a preferred embodiment

FIG. 2 shows a device 200 that can control a temperature of the fluid 150. The device 200 connects to the inlet 160 and outlet 170 of the molding lens 100 via tubes 210. The device 200 includes at least a first tank 230, for example for containing a liquid. Thermal elements that are in contact with the first tank 230 can heat and cool the liquid. The thermal elements include resistors or cooling elements, e.g., thermoelectric elements, used to heat or cool the liquid as needed. Temperature sensors, e.g., thermocouples, thermistors or intergraded circuits for temperature measurement, are used to detect a temperature of the liquid.

In addition, multiple tanks could be used. For example a second tank 240 can contain a liquid such as hot water and the first tank 230 can contain cold water. In addition, a third tank 250 could be used where the first tank contains a high temperature liquid, the second contains a liquid with a temperature of about 45° C. and the third tank contains a cold liquid (see example 2 below).

The device 200 also includes a circulation system that includes a pump 260, valves 270 and the tubes 210 for the circulation of the liquid to the molding lens 100. The circulation system can include a closed circuit between the pump 260, the molding lens 100 and the tanks 230, 240, 250. The liquid 150 is preferably supplied by tubes 210, which can be thin and flexible, in a manner that the forces which are exerted from the tubes 210 to the molding lens 100, during its placement over the cornea, is minimal.

The device 200 also includes an electronic control system 280 that includes an electric circuit for the temperature and flow control of the liquid 150. The electronic control system 280 preferably controls the thermal and cooling elements as well as the operation of the pump 260 and valves 270. When there is more than one tank 230, 240, 250, the electronic control system 280 controls the transfer valve 270 between the different tanks to transfer in the liquid 150 of desirable temperature to the molding lens 100.

It can be appreciated that the molding lens 100 may be covered with a substance, such as thermoreversible hydrogel, in the solid or liquid state. If a solid hydrogel is applied to the molding lens 100, the molding lens 100 can be heated to soften the hydrogel before applying the hydrogel to the cornea.

Figure 3:
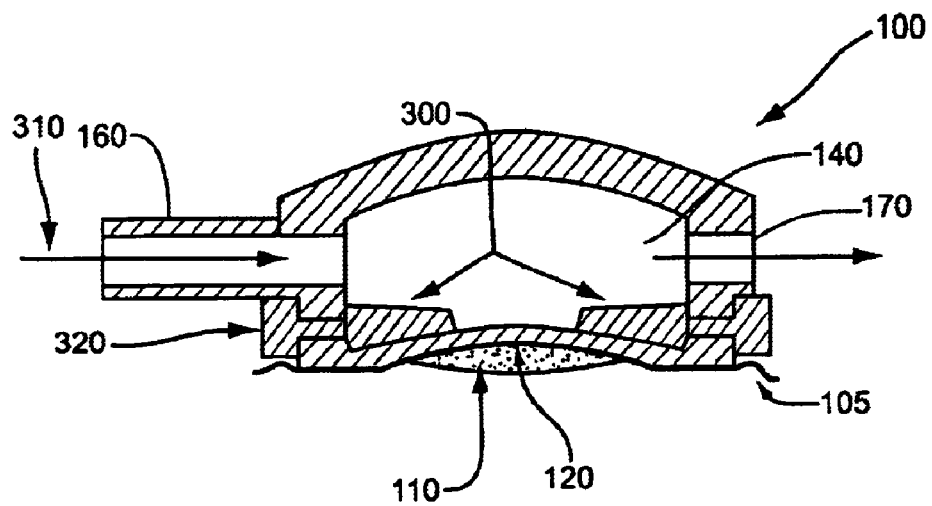
FIG. 3 shows a molding lens including a heating element according to a preferred embodiment.

FIG. 3 shows a molding lens 100 according to another preferred embodiment, the molding lens 100 further includes a heating element 300, for example resistors, inductors or capacitors, located near the molding surface 120. The heating element 300 heats the molding surface 120 and the molding surface 120 heats the substance 110, such as hydrogel, located near the molding surface 120. To cool the molding surface 120, and therefore cool the substance 110, a liquid or a gas 310 can be circulated through the cavity 140 via the inlet 160 and the outlet 170. Gases that can be circulated through the cavity include liquid nitrogen and carbon dioxide. External elements such as the cooler ambient air, or other low temperature gases, can also be used to cool the molding surface 120. Conductors 320 supply electrical energy to the heating element 300 proportional to the amount of heat required from the heating element 300.

Figure 4:
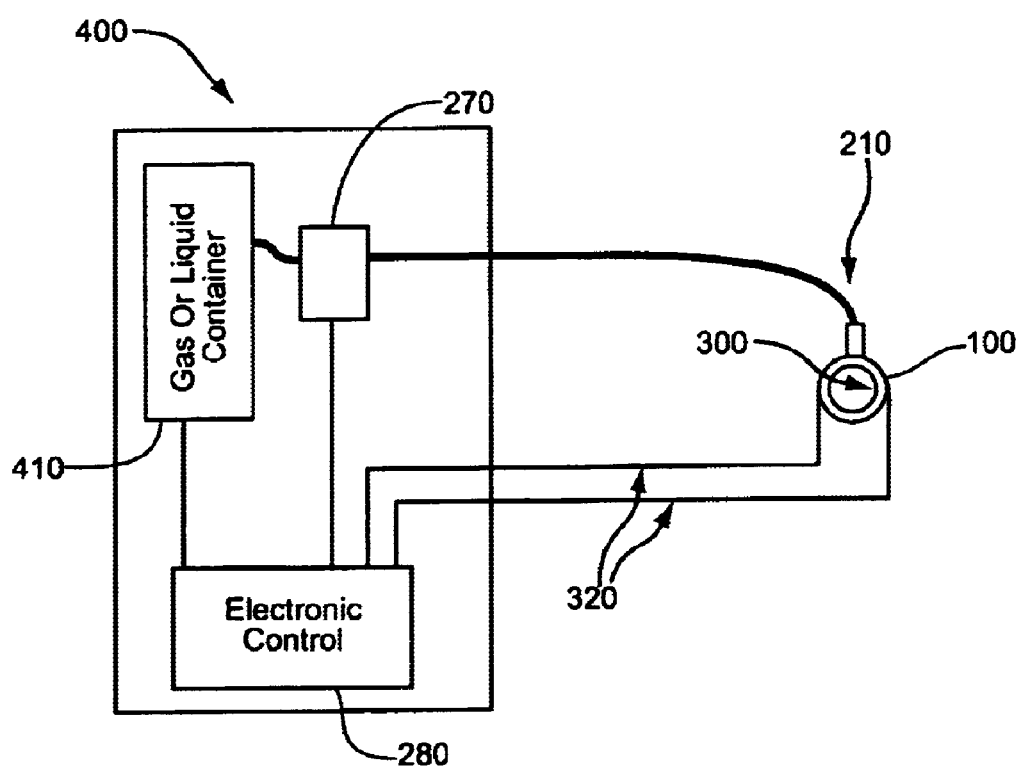
FIG. 4 shows a system for controlling the temperature of the molding lens of FIG. 3.

FIG. 4 shows a device 400 for controlling the heating and cooling of the molding lens 100. The device 400 includes a container 410 that contains a cooling gas or liquid. The electronic control system 280 controls the valve 270 to supply the gas or liquid to and from the molding lens 100 via the tubes 210. The electronic control system 280 also controls electrical flow to the heating element 300 via the conductors 320.

Figure 5:
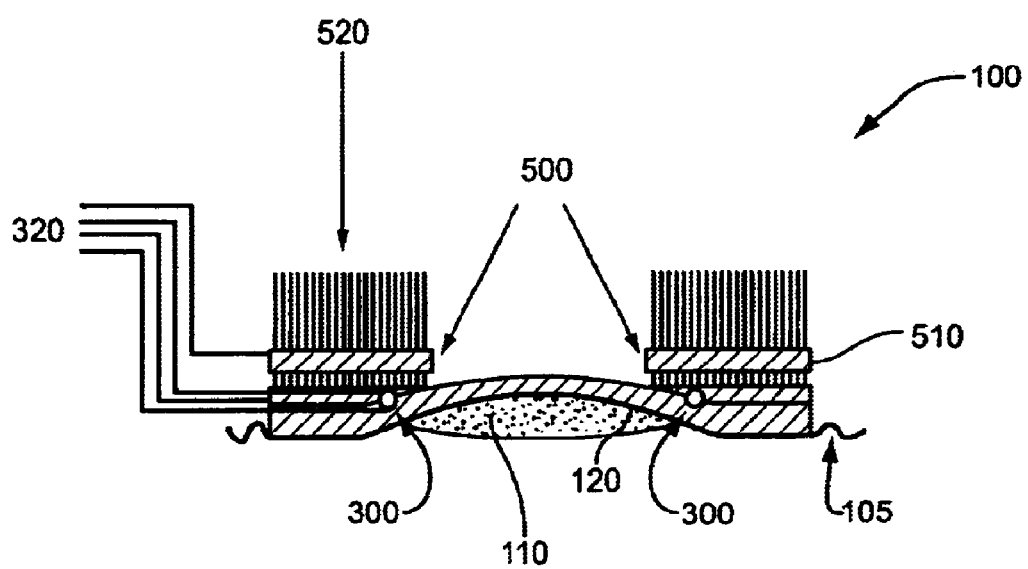
FIG. 5 shows a molding lens including an alternate heating element according to a preferred embodiment.

FIG. 5 shows another embodiment of the molding lens 100 including thermoelectric elements 500 (Peltier), such as a heat pump 510 and convector 520, in contact with the molding surface 120 to control the temperature of the molding surface 120. The conductors 320 that supply power to the thermoelectric elements 500 are preferably as thin and flexible as possible. The thermoelectric elements 500 cool down or heat up when supplied by direct voltage. The temperature at which the thermoelectric elements 500 cool or heat the molding surface 120 is proportional to the applied voltage. The polarity of the voltage proportionally changes behavior of the thermoelectric elements 500 from cooling to heating, and visa versa. Heating elements 300 located near the molding surface 120 can also be used to control the temperature of the molding surface 120, and thus the temperature of the substance 110.

In operation, the molding lens 100 can include a molding surface 120 such that the substance 110, for example the hydrogel, includes an optical zone diameter 5.5–11.0 mm, a transitional zone and a base curvature of curvature 7–11 mm. In addition, the molding lens 100 preferably includes at least one mark for their centering the molding lens 100. The molding lens 100 may also include other features, such as forceps sockets, for handling the molding lens 100. Referring again to FIG. 1, an external surface 180 of the molding lens 100 may be convex in shape to avoid the formation of reflections from the light of the surgical microscope. Preferably, the external surface 180 also has spherical shape with radius of curvature about 10 mm and bears a mark in its center.

To center the molding lens 100, when the patient observes a light source, a point is marked on the cornea behind which point the reflection of the light source can be seen. While the patient observes the same light source, the mold is placed centrally with the help of the mark which the molding lens 100 bears in the convex surface and at the same time the molding lens 100 is rotated such that the reflection of the light source from the convex surface of the mold coincides with the mark on the cornea. In a preferred embodiment the light source is the lamp of a surgical microscope. The molding surface of the mold may be covered with a thin, smooth membrane that can be easily detached from the mold. The membrane allows for easier removal of the mold from the solidified surface of the hydrogel and can be removed afterwards if so desired.

The following examples are used to show how aspects of the invention can be used in practice, but the invention should not be limited to these examples.

MATERIALIZATION EXAMPLE 1

The molding lens 100 includes a cylinder having a height of about 3 mm including an inner diameter size of about 8 mm and outer diameter size of about 11 mm. Lenses of a generally meniscus shape enclose the ends of the cylinder so that the concave surfaces of the lenses face the same direction. A first convex surface 190 of the molding lens 100 bears a mark used for the centering. A second concave surface, for example molding surface 120, is used to accommodate the molding. In this way a composite hollow lens is constructed, which has two concave external surfaces, one concave external surface and one convex external surface. Water or other suitable fluid 150 is supplied through thin and flexible tubes 160, 170. The fluid 150 enters the composite lens through holes in the cylinder and circulates in the cavity of the lens. The circulation is included within a closed circuit and the temperature of the circulating fluid is controlled from a device 200, 400 located outside the lens.

A modulator is formed with the help of this mold, as follows. When the patient observes a light source, a mark is made on the cornea at the point behind which the reflection of the light source can be seen. Water of a temperature of about 45° C. circulates in the inner of the mold. Heated hydrogel is placed on the surface of the cornea. While the patient observes the same light source through the mold, the mold is placed centrally with the help of the mark that the mold bears on its convex surface. The mold is rotated so that the image of the light source that is formed from the convex surface of the mold coincides with the mark that was made on the cornea.

When the centering procedure is complete, cool water is supplied to the molding lens 100 resulting in a solidification of the hydrogel. Thereafter, the molding lens 100 is removed, and a shaped quantity of hydrogel remains in the central region of the corneal surface, while the excess quantity of hydrogel is removed to the periphery.

MATERIALIZATION EXAMPLE 2

To form a modulator with the help of the mold, when the patient observes a light source, a mark is made on the cornea at the point behind which the reflection of the light source can be seen. The mold includes a membrane from polyethylene on the concave molding surface. The membrane includes a coated quantity of thermoreversible fluorescent hydrogel in a rigid form. Water of a high temperature is circulated inside the cavity of the mold for several minutes and the coated rigid hydrogel is liquefied.

Thereafter, water of a temperature of about 45° C. continues circulating in the cavity of the mold to keep the hydrogel in liquid form until the time of application. While the patient observes the light source through the mold, the mold is placed centrally with the help of the mark that the mold bears on its convex surface. Also, the mold is rotated so that the image of the light source that is formed from the convex surface of the mold coincides with the mark that was made on the cornea.

When the centering procedure is complete, cool water is supplied into the inner of the mold resulting in solidification of the hydrogel. The mold and the polyethylene membrane are removed. A shaped quantity of hydrogel remains in the central region of the corneal surface while the excess quantity of the hydrogel has been expelled to the periphery.

MATERIALIZATION EXAMPLE 3

The cavity of the molding lens 100 includes heating elements 300, 500, e.g. electric resistive elements. On the external surface of the mold there are junctions through which the electric current enters the heating elements 300, 500. The mold is heated up when electric current is switched on. To cool the molding lens 100 and substance located on the molding lens, such as hydrogel, a low temperature liquid or gas, for example liquid nitrogen or $CO_2$, may be inserted through this socket in the cavity.

To form the modulator with the help of this mold, when the patient observes a light source, a mark is made on the cornea at the point behind which the reflection of the light source can be seen. The mold includes a membrane of polyethylene located on the concave molding surface. On the membrane there is coated a quantity of thermoreversible fluorescent hydrogel in rigid form. A current is supplied in the heating elements 300, 500 in the mold for a time needed to liquefy the rigid hydrogel.

A lower intensity electric current continues supplying the heating elements 300, 500 to maintain a stable temperature to keep the hydrogel in liquid form until the time of application. While the patient observes the light source through the mold, the mold is placed centrally with the help of the mark which the mold bears on its convex surface, and at the same time the mold is rotated so that the image of the light source which is formed from the convex surface of the mold coincides with the mark which was made on the cornea.

When the procedure of centering is complete, electric current is switched off, and a low temperature gas, e.g. liquid nitrogen, is supplied to the cavity in order to solidify the hydrogel. The mold is removed, then the polyethylene membrane is removed, and a shaped quantity of hydrogel remains in the central region of the corneal surface while the excess quantity of hydrogel is expelled to the periphery.

While the invention has been described above by reference to various embodiments, it will be understood that many changes and modifications can be made without departing from the scope of the invention. It is therefore intended that the foregoing detailed description be understood as an illustration of the presently preferred embodiments of the invention, and not as a definition of the invention. It is only the following claims, including all equivalents, which are intended to define the scope of this invention.

We claim:

1. A device for correcting imperfections of a cornea of an eye, the device comprising:
   a) a molding lens, wherein the molding lens includes an internal surface and an external surface, wherein the external surface includes a concave shape to correspond to a desired shape of the cornea, wherein the external surface of the molding lens is operable to be placed on the cornea of the eye, and wherein the external surface is operable to receive a substance; and
   b) a membrane, wherein the membrane covers the external surface of the molding lens and wherein the substance is positionable on the membrane; and
   c) an element attached to the molding lens to control a temperature of the external surface of the molding lens, wherein the element is capable of supplying at least one of a fluid and a gas to the internal surface of the molding lens, and wherein the element is capable of causing the substance applied to the molding lens to be solidified and liquefied.

2. The device according to claim 1 wherein the temperature of the external surface of the molding lens is controlled between approximately 0 and approximately 55 degrees Celsius.

3. The device according to claim 1 further including a control device to control the temperature.

4. The device according to claim 3 wherein the control device includes electronic circuitry.

5. The device according to claim 3, wherein the control of the temperature is implemented by supplying a fluid which contacts the interior surface of the molding lens and wherein the fluid temperature and flow are controlled by the control device.

6. The device according to claim 1 wherein cooling of the molding lens is implemented by a flow of cool gas by the molding lens.

7. The device according to claim 1, further including tubes, wherein the fluid is supplied to the internal surface of the molding lens through the tubes.

8. The device according to claim 1, wherein the control of the temperature is implemented by a flow of gas with controllable temperature through the molding lens.

9. The device according to claim 1 wherein the substance can be liquefied upon heating.

10. The device according to claim 1 wherein the membrane comprises polyethylene.

11. The device according to claim 1 wherein the substance comprises a thermoreversible hydrogel.

12. The device of claim 11 wherein the thermoreversible hydrogel is maintained in a liquid state by using the element to apply heat to the external surface of the molding lens.

13. The device of claim 11 wherein the thermoreversible hydrogel is solidified by using the element to cool the external surface of the molding lens.

14. The device of claim 13 wherein when the molding lens is removed from the cornea of the eye a solid thermoreversible hydrogel remains in situ.

15. The device of claim 1 wherein the membrane is capable of being removed from the molding lens.

* * * * *

UNITED STATES PATENT AND TRADEMARK OFFICE
CERTIFICATE OF CORRECTION

PATENT NO. : 6,723,089 B2
DATED : April 20, 2004
INVENTOR(S) : Ioannis Pallikaris et al.

It is certified that error appears in the above-identified patent and that said Letters Patent is hereby corrected as shown below:

Title page,
Item [65], Prior Publication Data, insert the following:
-- US 2000/0100144    April 21, 2001 --.

Column 8,
Line 42, insert claims 16 and 17 as follows:
-- 16. The device accroding to claim 1 wherein the cooling element acts to solidify the substance.

17. The device according to claim 1, wherein the element liquefies the substance before the molding lens has been positioned in contact with the cornea and solidifies the substance after the molding lens has been positioned in contact with the cornea. --

Signed and Sealed this

Tenth Day of May, 2005

JON W. DUDAS
*Director of the United States Patent and Trademark Office*